US012728415B2

(12) United States Patent
Esch

(10) Patent No.: US 12,728,415 B2
(45) Date of Patent: Sep. 8, 2026

(54) GRAVITY FLOW MICRO-PHYSIOLOGICAL ARTICLE AND DETERMINING A PHYSIOLOGICAL RESPONSE TO A DRUG

(71) Applicant: Government of the United States of America, as represented by the Secretary of Commerce, Gaithersburg, MD (US)

(72) Inventor: Mandy Brigitte Esch, Gaithersburg, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 834 days.

(21) Appl. No.: 17/513,942

(22) Filed: Oct. 29, 2021

(65) Prior Publication Data

US 2022/0134331 A1 May 5, 2022

Related U.S. Application Data

(60) Provisional application No. 63/107,466, filed on Oct. 30, 2020.

(51) Int. Cl.
*B01L 3/00* (2006.01)
*G01N 33/50* (2006.01)

(52) U.S. Cl.
CPC ..... *B01L 3/50273* (2013.01); *B01L 3/502715* (2013.01); *G01N 33/5038* (2013.01); *B01L 2400/0457* (2013.01)

(58) Field of Classification Search
CPC ............ B01L 3/50273; B01L 2200/12; B01L 3/502707; B01L 2200/0647; B01L 2300/046; B01L 2300/06; B01L 2300/0609; B01L 2300/0867; B01L 2300/0887; B01L 2300/0896; B01L 2400/0415; B01L 9/00; B01L 3/502715; B01L 2200/0652; B01L 2200/10; B01L 2300/0663; B01L 2300/0861; B01L 2400/0439; B01L 3/502; B01L 2200/0663; B01L 2200/0668; B01L 2300/0819; B01L 2400/043; B01L 2400/0457; B01L 3/502738; B01L 3/502761; B01L 2300/0645; G01N 27/44791; G01N 1/28; G01N 2223/307; G01N 21/031; G01N 21/255; G01N 21/27; G01N 21/84; G01N 2291/0255; G01N 2291/0256; G01N 15/1023; G01N 21/94; G01N 2500/10; C12M 23/16; C12M 25/06; C12M 27/10
See application file for complete search history.

(56) References Cited

U.S. PATENT DOCUMENTS

| | | | | |
|---|---|---|---|---|
| 2016/0107160 A1* | 4/2016 | Desmond | .......... | B01L 3/502753 422/502 |
| 2018/0273888 A1* | 9/2018 | Esch | ...................... | C12M 21/08 |
| 2019/0106665 A1* | 4/2019 | Ingber | .................... | C12M 35/08 |

* cited by examiner

*Primary Examiner* — Dean Kwak
(74) *Attorney, Agent, or Firm* — Office of Chief Counsel for National Institute of Standards and Technology

(57) ABSTRACT

A gravity flow micro-physiological article determines a physiological response to a drug and includes: supply chambers; a mixing chamber; and a liquid divider, wherein the divider divides fluid under gravitational force so that individual portions of the fluid independently include metabolites in a proportionate amount as physically determined by the liquid divider.

12 Claims, 12 Drawing Sheets

GRAVITY FLOW MICRO-PHYSIOLOGICAL ARTICLE AND DETERMINING A PHYSIOLOGICAL RESPONSE TO A DRUG

CROSS REFERENCE TO RELATED APPLICATIONS

This application claims the benefit of U.S. Provisional Patent Application Ser. No. 63/107,466 (filed Oct. 30, 2020), which is herein incorporated by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in this invention.

BRIEF DESCRIPTION

Disclosed is a gravity flow micro-physiological article for determining a physiological response to a drug, the gravity flow micro-physiological article comprising: a substrate; a first supply chamber disposed on the substrate and that provides a first supply fluid flow; a second supply chamber disposed on the substrate and that provides a second supply fluid flow, such that the first supply fluid flow from the first supply chamber is parallel to the second supply fluid flow from the second supply chamber; a mixing chamber in fluid communication with the first supply chamber and the second supply chamber and that: receives the first supply fluid flow from the first supply chamber; receives the second supply fluid flow from the second supply chamber; and combines the first supply fluid flow and the second supply fluid flow to form a combined fluid flow; a liquid divider in fluid communication with the mixing chamber and that: receives the combined fluid flow from the mixing chamber; and divides the combined fluid flow into a first divided fluid flow and a second divided fluid flow, wherein the liquid divider is in fluid communication with the first supply chamber and the second supply chamber such that: the first supply chamber receives the first divided fluid flow from the liquid divider; and the second supply chamber receives the second divided fluid flow from the liquid divider.

Disclosed is a process for determining a physiological response to a drug with a gravity flow micro-physiological article, the process comprising: disposing a first biological cell in a first supply chamber of the gravity flow micro-physiological article; disposing a second biological cell in a second supply chamber of the gravity flow micro-physiological article; disposing a blood surrogate in a liquid divider of the gravity flow micro-physiological article, the blood surrogate comprising the drug; subjecting the gravity flow micro-physiological article to movement to divide the blood surrogate into a first divided fluid flow and a second divided fluid flow of the gravity flow micro-physiological article, wherein the first divided fluid flow and the second divided fluid flow independently comprise a portion of the blood surrogate in a proportionate amount as physically determined by the divider of the gravity flow micro-physiological article; communicating the first divided fluid flow to the first supply chamber; receiving, by the first supply chamber, the first divided fluid flow from a first return fluid chamber of the gravity flow micro-physiological article; communicating the second divided fluid flow to the second supply chamber; receiving, by the second supply chamber, the second divided fluid flow from a second return fluid chamber of the gravity flow micro-physiological article; contacting; in the first supply chamber, the first biological cell with the drug in the first divided fluid flow; producing a first metabolite from the first biological cell in response to contact with the drug in the first divided fluid flow; contacting, in the second supply chamber, the second biological cell with the drug in the second divided fluid flow; producing a second metabolite from the second biological cell in response to contact with the drug in the second divided fluid flow; producing, by the first supply chamber, a first supply fluid flow that comprises the first metabolite; producing, by the second supply chamber, a second supply fluid flow that comprises the second metabolite; communicating, in parallel to a mixing chamber, the first supply fluid flow from the first supply chamber and the second supply fluid flow from the second supply chamber; receiving, by the mixing chamber, in parallel, the first supply fluid flow and the second supply fluid flow; combining, by the mixing chamber, the first supply fluid flow and the second supply fluid flow to produce a combined fluid flow that comprises the first metabolite and the second metabolite; communicating, from the mixing chamber, the combined fluid flow; receiving, by the liquid divider, the combined fluid flow from the mixing chamber; and dividing, under gravitational force, the combined fluid flow into the first divided fluid flow and the second divided fluid flow, wherein the first divided fluid flow and the second divided fluid flow independently comprise of the first metabolite and the second metabolite in a proportionate amount as physically determined by the divider to determine independently the physiological response of the first biological cell and the second biological cell to the drug.

BRIEF DESCRIPTION OF THE DRAWINGS

The following description cannot be considered limiting in any way. Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

A detailed description of one or more embodiments is presented herein by way of exemplification and not limitation.

It has been discovered that gravity flow micro-physiological article 200 is a microphysiological system that operates as an open microfluidic system. Fluidic flow is achieved via gravity, and physiologic fluid residence times are achieved by placing gravity flow micro-physiological article 200 at various angles, e.g., by a rotating or rocking gravity flow micro-physiological article 200. Gravity flow micro-physiological article 200 can include near-physiologic amounts of a blood surrogate.

Gravity flow micro-physiological article 200 overcomes technological impairments with conventional microphysiological systems. Exemplary problems with conventional microphysiological systems that are overcome by gravity flow micro-physiological article 200 include insensitivity of conventional systems to toxic metabolites in biological fluid (e.g., a blood surrogate) due to dilution of toxic metabolites in an excess volume of fluid carrier; unreliability of conventional microphysiological systems with respect to tissue death caused by sample leakage by the conventional microphysiological systems; uptake of air bubbles in a blood surrogate in a flow of the blood surrogate in the conventional microphysiological systems; and failure of conventional microphysiological systems because active components (e.g., a pump, valve, and the like) of the conventional microphysiological systems that cease to function.

Figure 1:
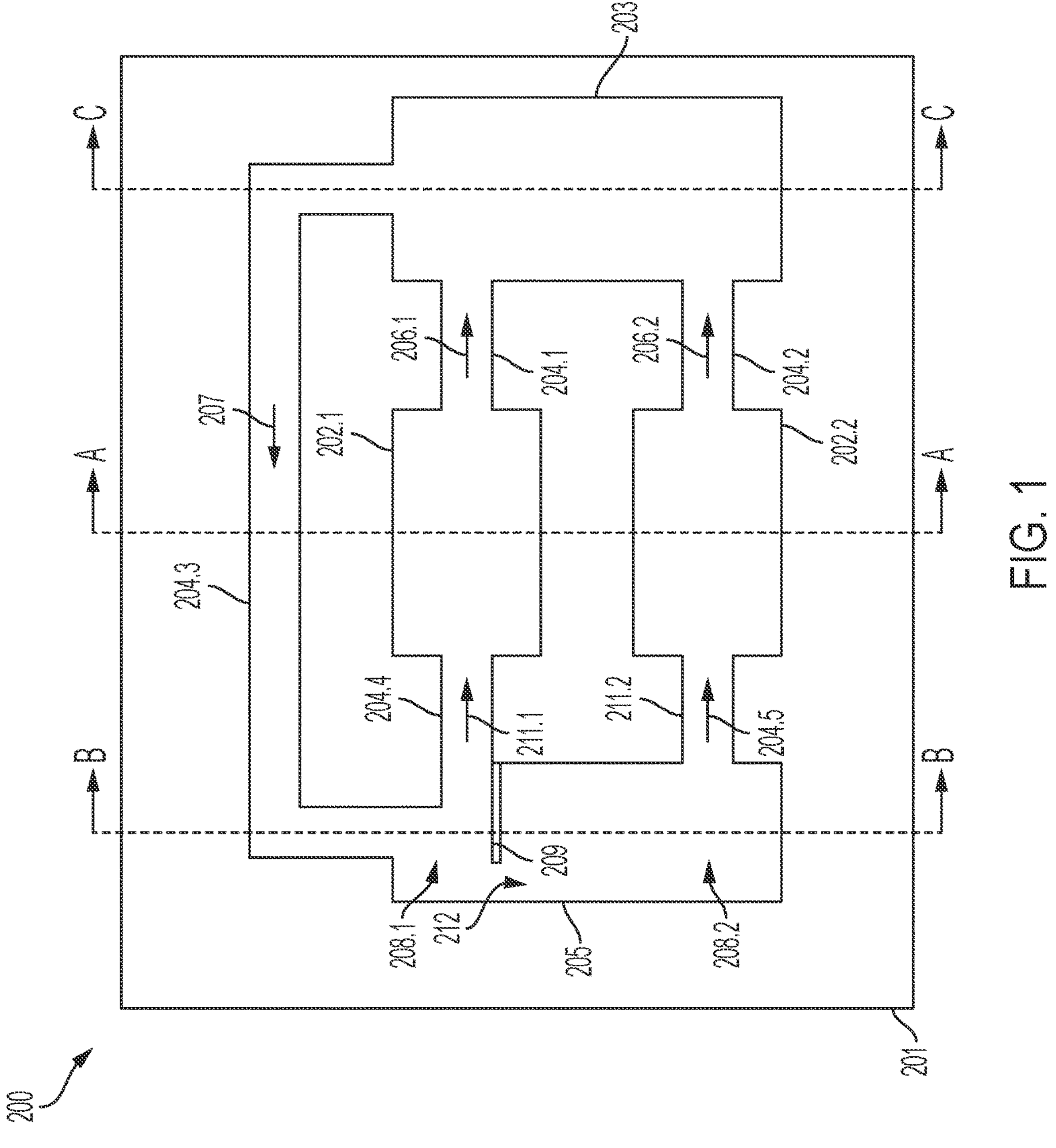
FIG. 1 shows gravity flow micro-physiological article, according to some embodiments.
Figure 2:
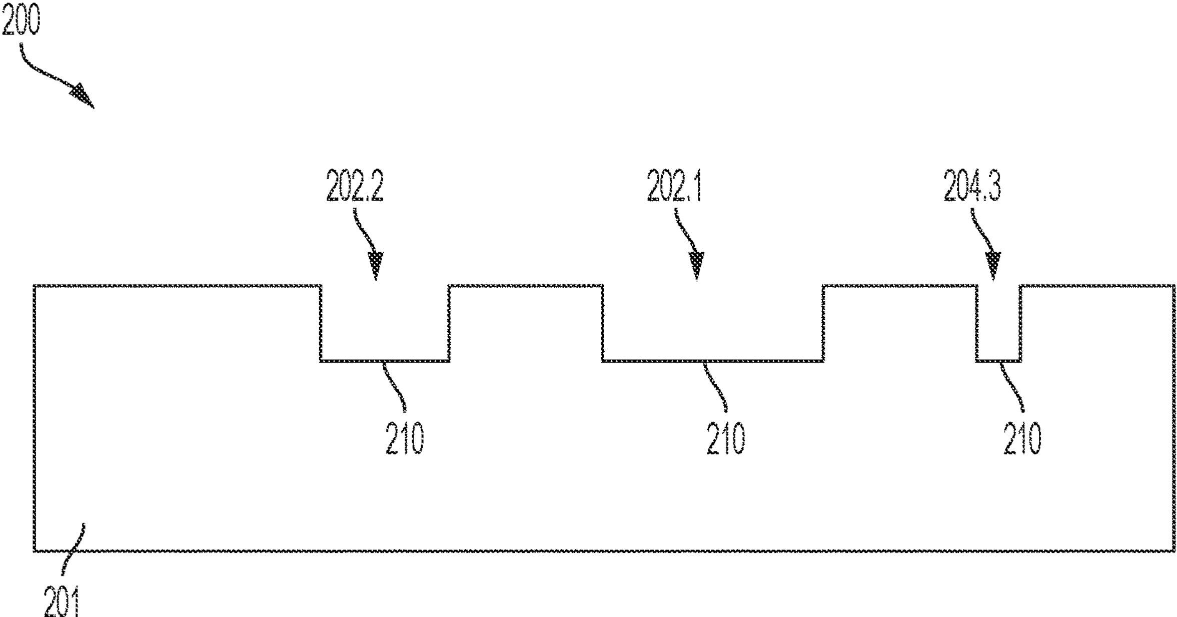
FIG. 2 shows a cross-section along line A-A of gravity flow micro-physiological article shown in FIG. 1, according to some embodiments.
Figure 3:
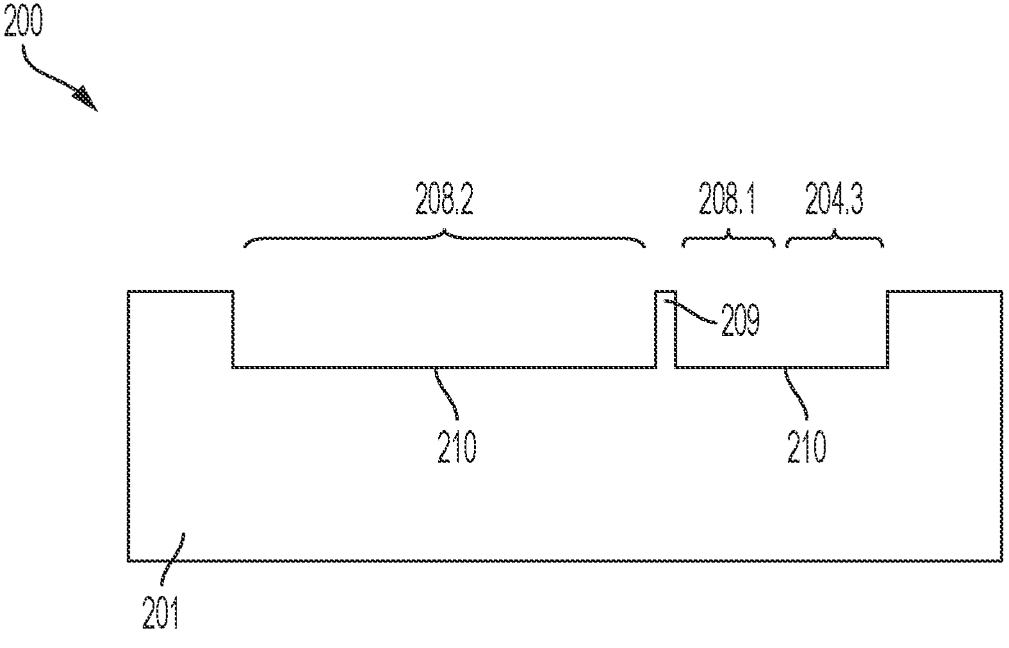
FIG. 3 shows a cross-section along line B-B of gravity flow micro-physiological article shown in FIG. 1, according to some embodiments.
Figure 4:
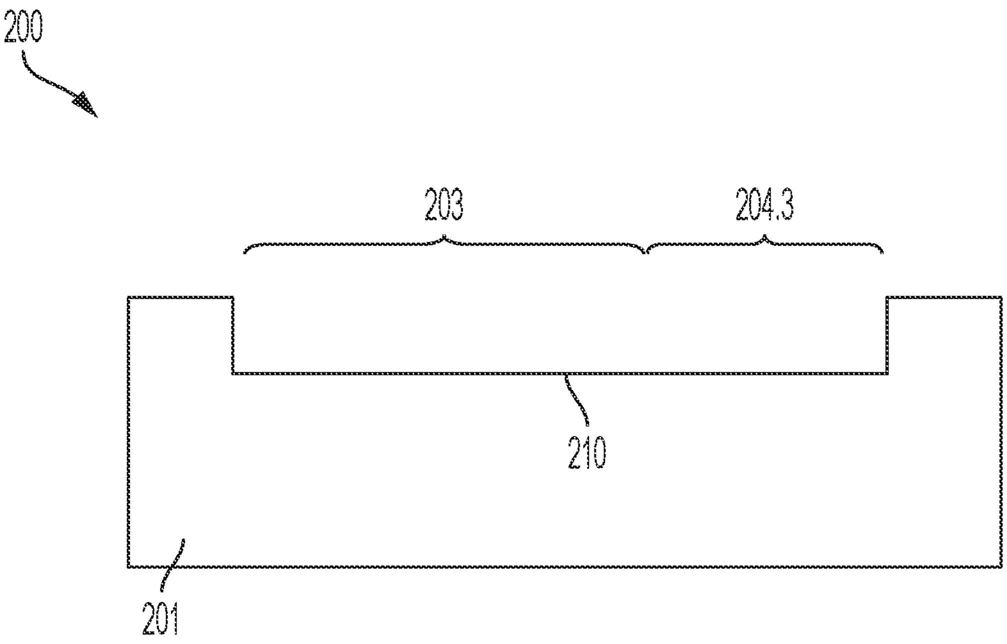
FIG. 4 shows a cross-section along line C-C of gravity flow micro-physiological article shown in FIG. 1, according to some embodiments.
Figure 5:
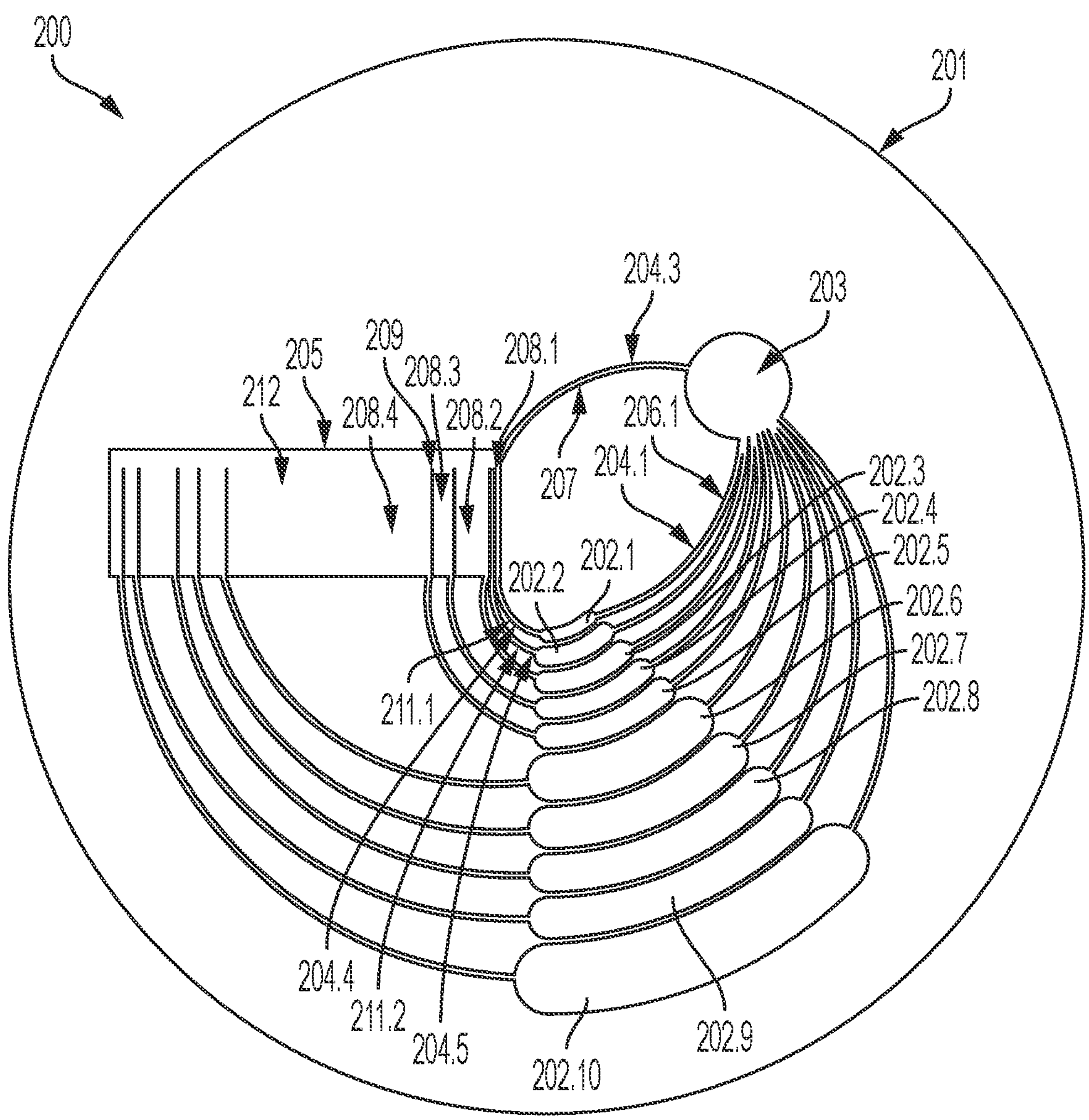
FIG. 5 shows a gravity flow micro-physiological article, according to some embodiments.
Figure 6:
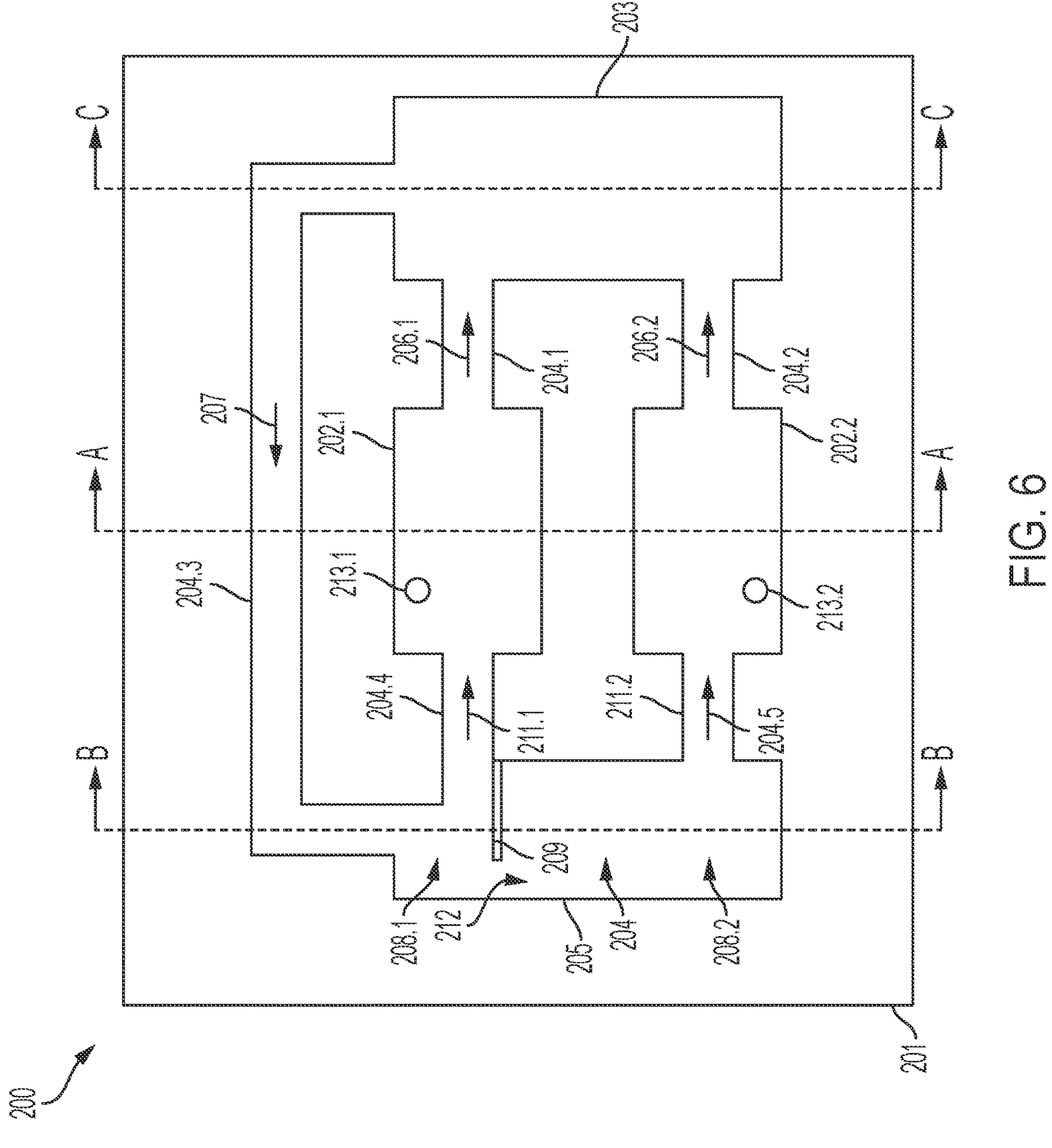
FIG. 6 shows a gravity flow micro-physiological article with a biological cell disposed in a supply chamber, according to some embodiments.
Figure 7:
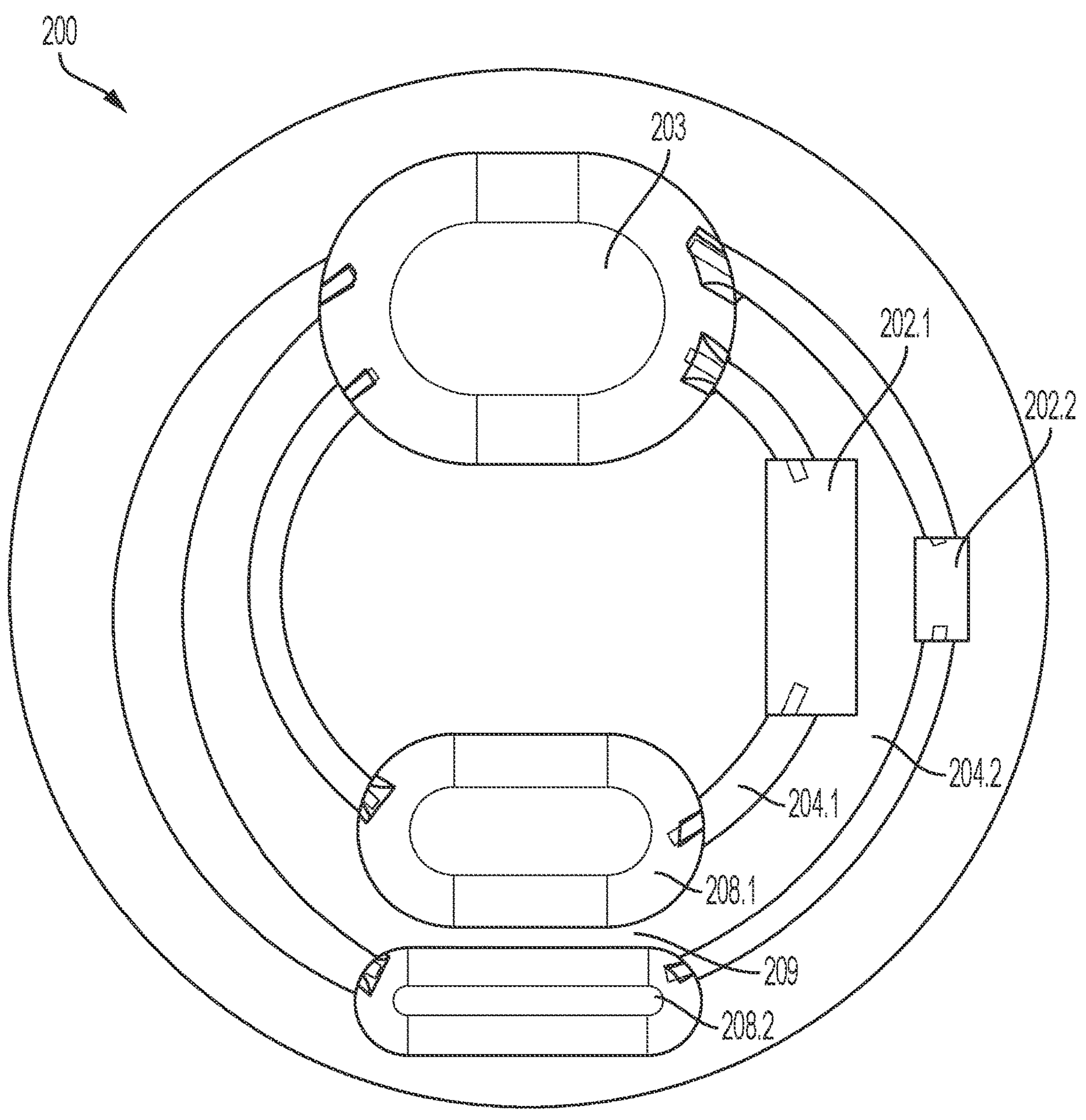
FIG. 7 shows a gravity flow micro-physiological article, according to some embodiments.
Figure 8:
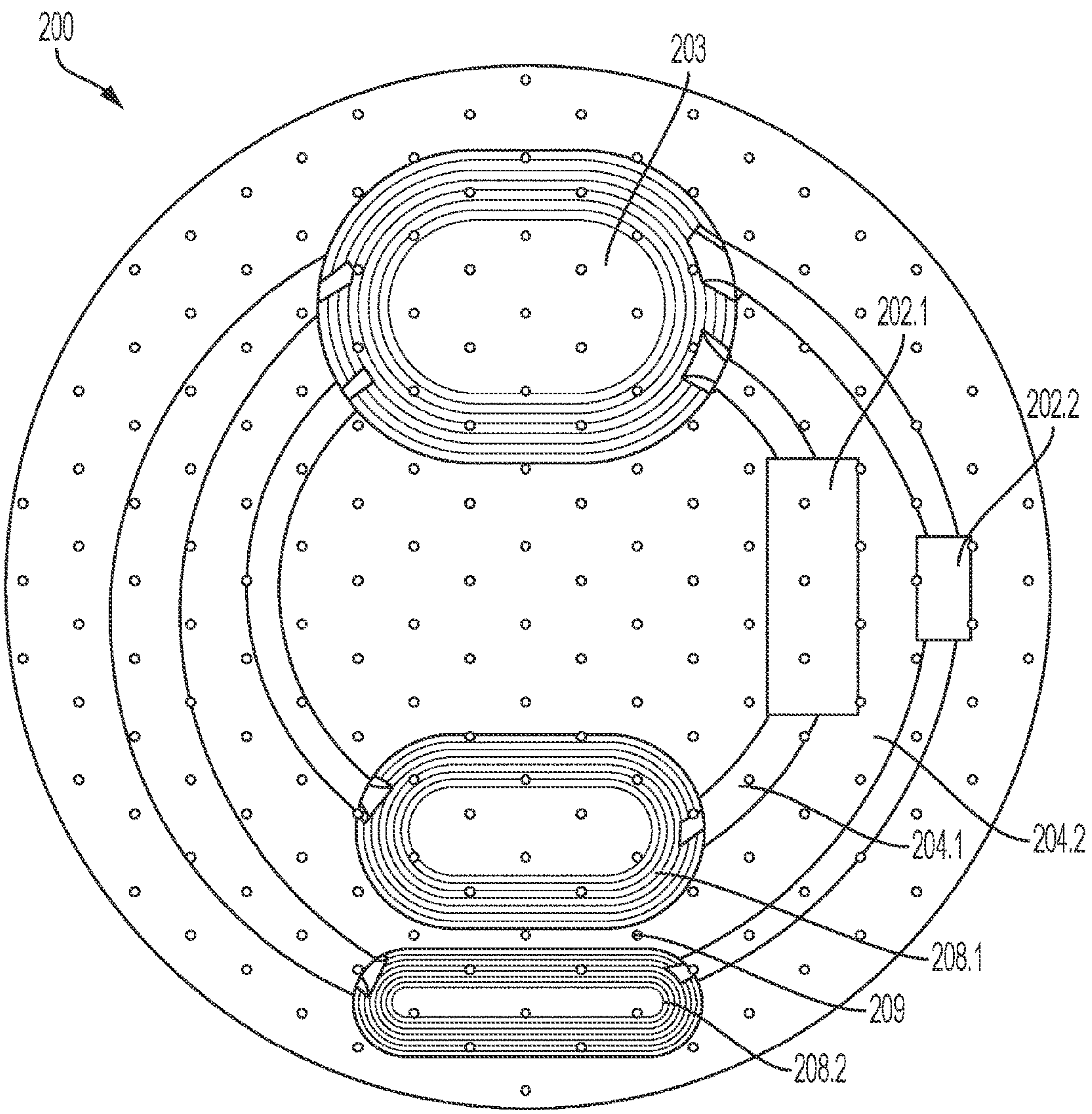
FIG. 8 shows a picture of the gravity flow micro-physiological article shown in FIG. 7, according to some embodiments.
Figure 9:
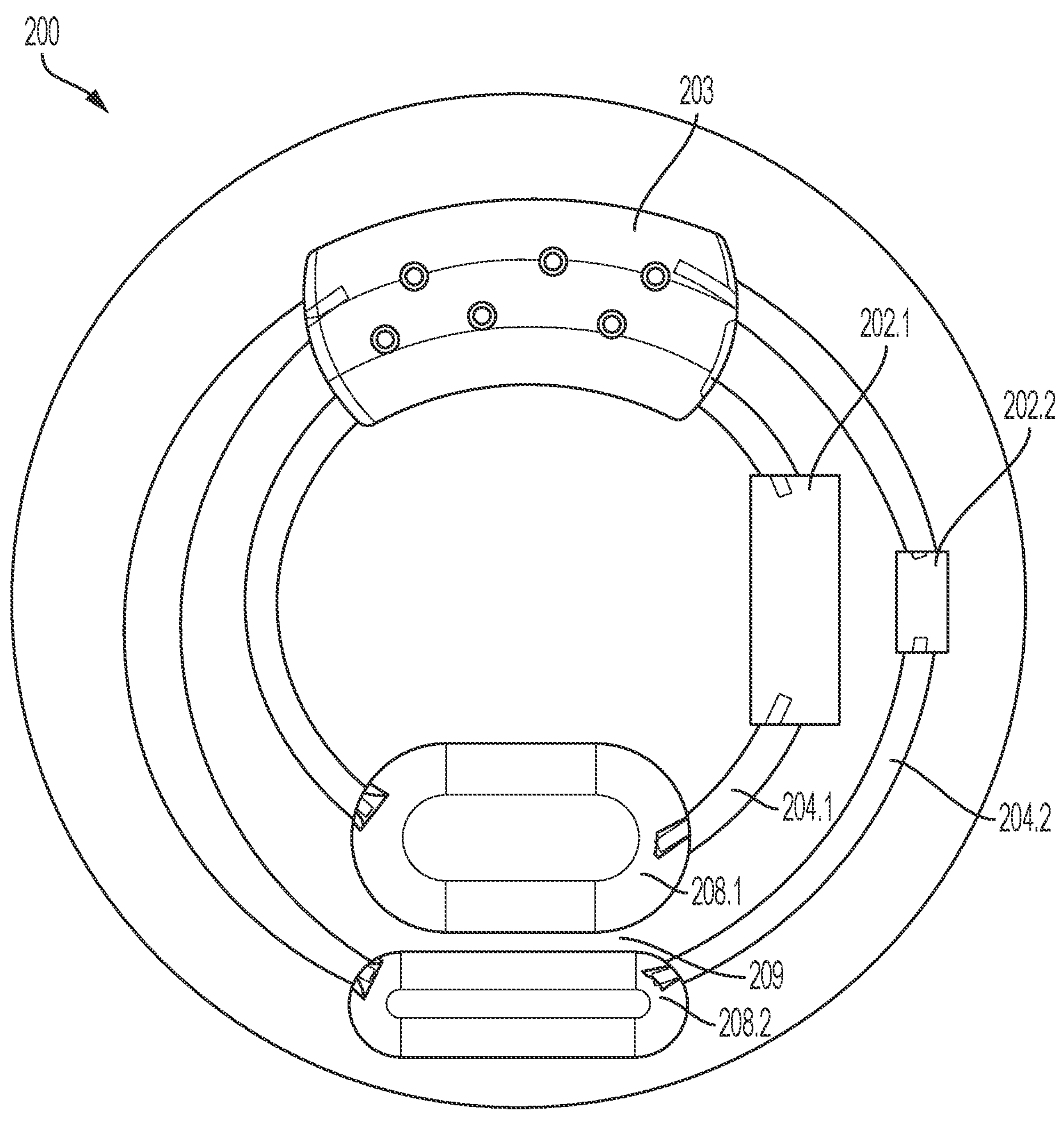
FIG. 9 shows a gravity flow micro-physiological article, according to some embodiments.
Figure 10:
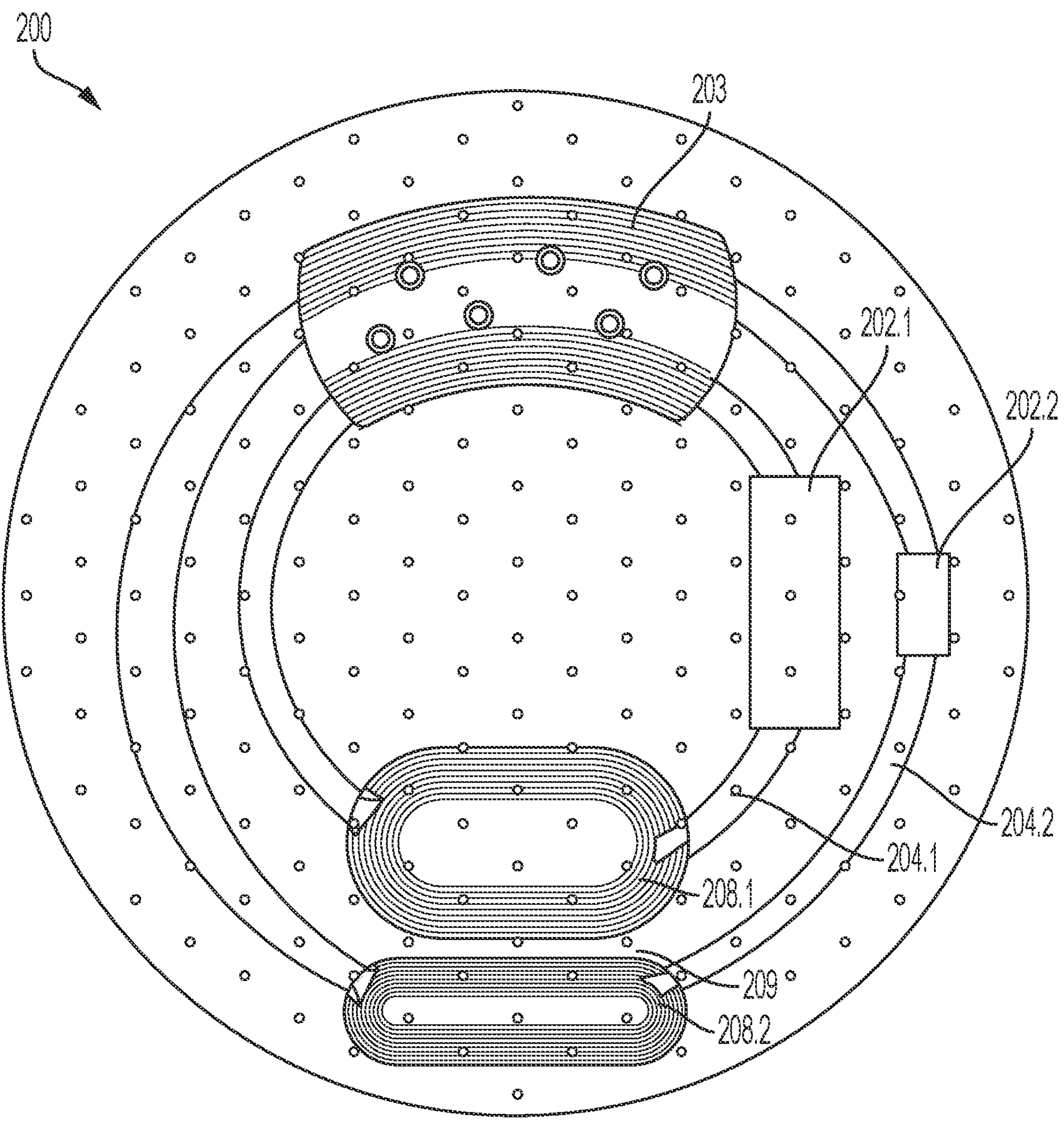
FIG. 10 shows a gravity flow micro-physiological article shown in FIG. 9, according to some embodiments.

Gravity flow micro-physiological article 200 determines a physiological response to a drug. In an embodiment, with reference to FIG. 1, FIG. 2, FIG. 3, FIG. 4; FIG. 5, FIG. 6, FIG. 7; FIG. 8, FIG. 9, and FIG. 10, gravity flow micro-physiological article 200 includes: a substrate 201; a first supply chamber 202.1 disposed on the substrate 201 and that provides a first supply fluid flow 206.1; a second supply chamber 202.1 disposed on the substrate 201 and that provides a second supply fluid flow 206.2, such that the first supply fluid flow 206.1 from the first supply chamber 202.1 is parallel to the second supply fluid flow 206.2 from the second supply chamber 202.2; a mixing chamber 203 in fluid communication with the first supply chamber 202.1 and the second supply chamber 202.2 and that: receives the first supply fluid flow 206.1 from the first supply chamber 202.1; receives the second supply fluid flow 206.2 from the second supply chamber 202.2; and combines the first supply fluid flow 206.1 and the second supply fluid flow 206.2 to form a combined fluid flow 207; a liquid divider 205 in fluid communication with the mixing chamber 203 and that: receives the combined fluid flow 207 from the mixing chamber 203; and divides the combined fluid flow 207 into a first divided fluid flow 211.1 and a second divided fluid flow 211.2; wherein the liquid divider 205 is in fluid communication with the first supply chamber 202.1 and the second supply chamber 202.2 such that: the first supply chamber 202.1 receives the first divided fluid flow 211.1 from the liquid divider 205; and the second supply chamber 202.1 receives the second divided fluid flow 211.2 from the liquid divider 205.

In an embodiment, the liquid divider 205 includes a divider 209 that partitions the liquid divider 205 into a plurality of return fluid chambers 208. In an embodiment, the return fluid chambers 208 comprises a first return fluid chamber 208.1, a second return fluid chamber 208.2, a third return fluid chamber 208.3, . . . , and an n-th return fluid chamber 208.*n*, wherein n is an integer that can be selected based on a number of supply chambers 202 disposed on the substrate 201 of the gravity flow micro-physiological article 200.

In an embodiment; gravity flow micro-physiological article 200 includes a plurality of flow channels 204 that fluidically interconnects the supply chamber 202, the mixing chamber 203, and the liquid divider 205 and provides fluid flow between the supply chamber 202, the mixing chamber 203, and the liquid divider 205.

In an embodiment, the first supply chamber 202.1 receives a first biological cell 213.1; the second supply chamber 202.2 receives a second biological cell 213.2; and the liquid divider 205 receives a blood surrogate 214 comprising the drug. In an embodiment, the gravity flow micro-physiological article 200 divides the blood surrogate 214 into a first divided fluid flow 211.1 and a second divided fluid flow 211.2 in response to the gravity flow micro-physiological article 200 being subjected to movement, wherein the first divided fluid flow 211.1 and the second divided fluid flow 211.2 independently comprise a portion of the blood surrogate 214 in a proportionate amount as physically determined by the divider 209. In an embodiment, the gravity flow micro-physiological article 200 communicates the first divided fluid flow 211.1 to the first supply chamber 202.1; the first supply chamber 202.1 receives the first divided fluid flow 211.1 from the first return fluid chamber 208.1; the gravity flow micro-physiological article 200 communicates the second divided fluid flow 211.2 to the second supply chamber 202.2; and the second supply chamber 202.2 receives the second divided fluid flow 211.2 from the second return fluid chamber 208.2 of the gravity flow micro-physiological article 200. In an embodiment, in the first supply chamber 202.1, the first biological cell 213.1 contacts the drug in the first divided fluid flow 211.1, so that a first metabolite 215.1 is produced by the first biological cell 213.1 in response to contact with the drug in the first divided fluid flow 211.1; and, in the second supply chamber 202.2, the second biological cell 213.2 contacts the drug in the second divided fluid flow 211.2, so that a second metabolite 215.2 is produced by the second biological cell 213.2 in response to contact with the drug in the second divided fluid flow 211.2. In an embodiment, the first supply chamber 202.1 produces a first supply fluid flow 206.1 that comprises the first metabolite 215.1; the second supply chamber 202.2 produces a second supply fluid flow 206.2 that comprises the second metabolite 215.2; and the first supply fluid flow 206.1 from the first supply chamber 202.1 and the second supply fluid flow 206.2 from the second supply chamber 202.2 are communicated in parallel to the mixing chamber 203. In an embodiment, the mixing chamber 203 receives, in parallel, the first supply fluid flow 206.1 and the second supply fluid flow 206.2; combines the first supply fluid flow 206.1 and the second supply fluid flow 206.2; produces a combined fluid flow 207 that comprises the first metabolite 215.1 and the second metabolite 215.2; and communicates the combined fluid flow 207 to the liquid divider 205. In an embodiment, the liquid divider 205 receives the combined fluid flow 207 from the mixing chamber 203; and divides, under gravitational force, the combined fluid flow 207 into the first divided fluid flow 211.1 and the second divided fluid flow 211.2, such that the first divided fluid flow 211.1 and the second divided fluid flow 211.2 independently comprise the first metabolite 215.1 and the second metabolite 215.2 in a proportionate amount as physically determined by the divider 209.

Gravity flow micro-physiological article 200 can be made in various ways. It should be appreciated that gravity flow micro-physiological article 200 includes a number of optical, electrical, or mechanical components, wherein such components can be interconnected and placed in communication (e.g., optical communication, electrical communication, mechanical communication, and the like) by physical, chemical, optical, or free-space interconnects. Elements of gravity flow micro-physiological article 200 can be formed from a polymer although other suitable materials, such ceramic, glass, or metal can be used. According to an embodiment, the elements of gravity flow micro-physiological article 200 are formed using 3D printing although the elements of gravity flow micro-physiological article 200 can be formed using other methods, such as injection molding or machining a stock material such as block of material that is subjected to removal of material such as by cutting, laser oblation, and the like. Accordingly, gravity flow micro-physiological article 200 can be made by additive or subtractive manufacturing. In an embodiment, elements of gravity flow micro-physiological article 200 are selectively etched to remove various different materials using different etchants and photolithographic masks and procedures. In some embodiments, various layers formed that are subjected to joining by bonding to form gravity flow micro-physiological article 200.

Figure 11:
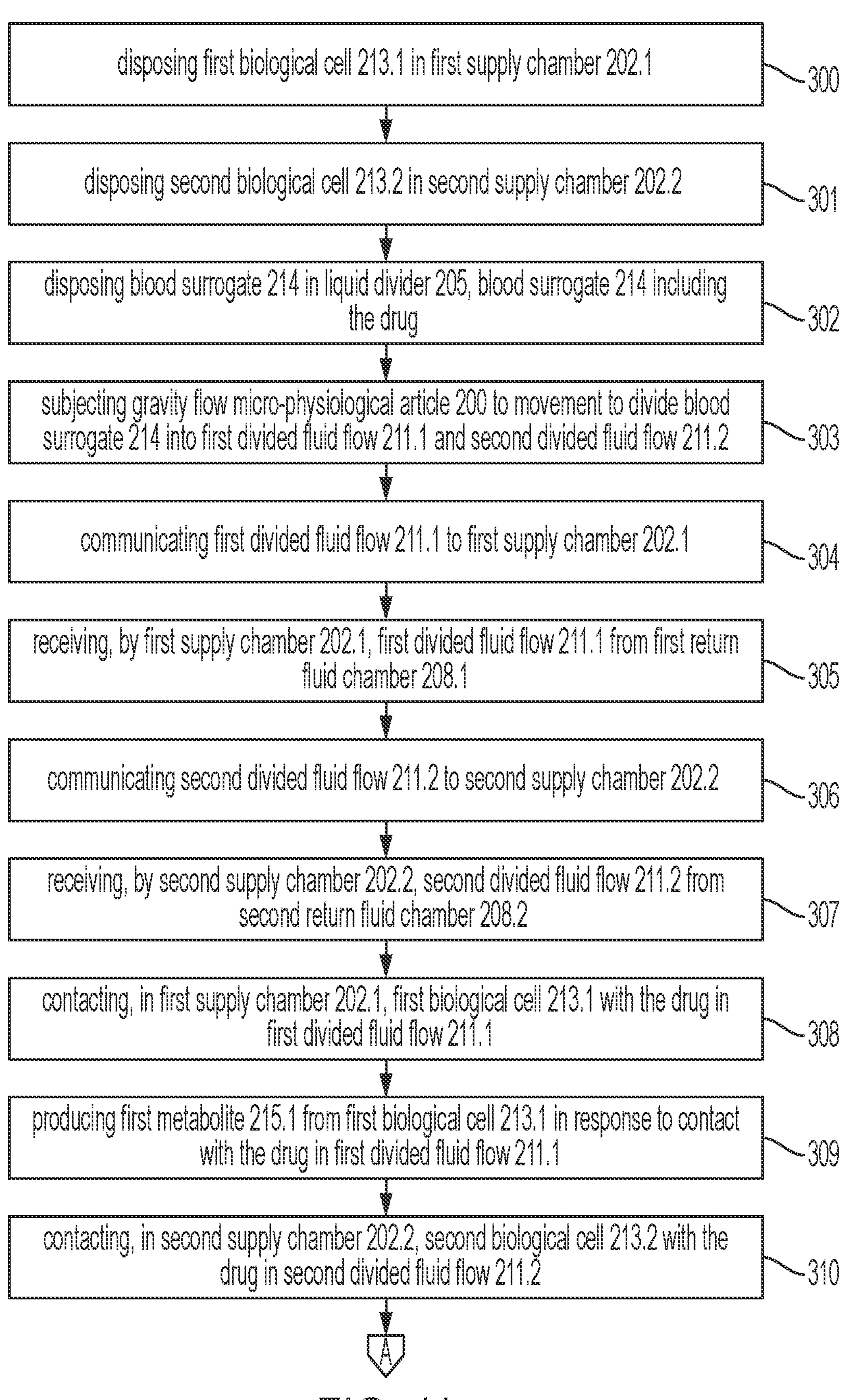
FIG. 11 shows steps in determining a physiological response to a drug, according to some embodiments.
Figure 12:
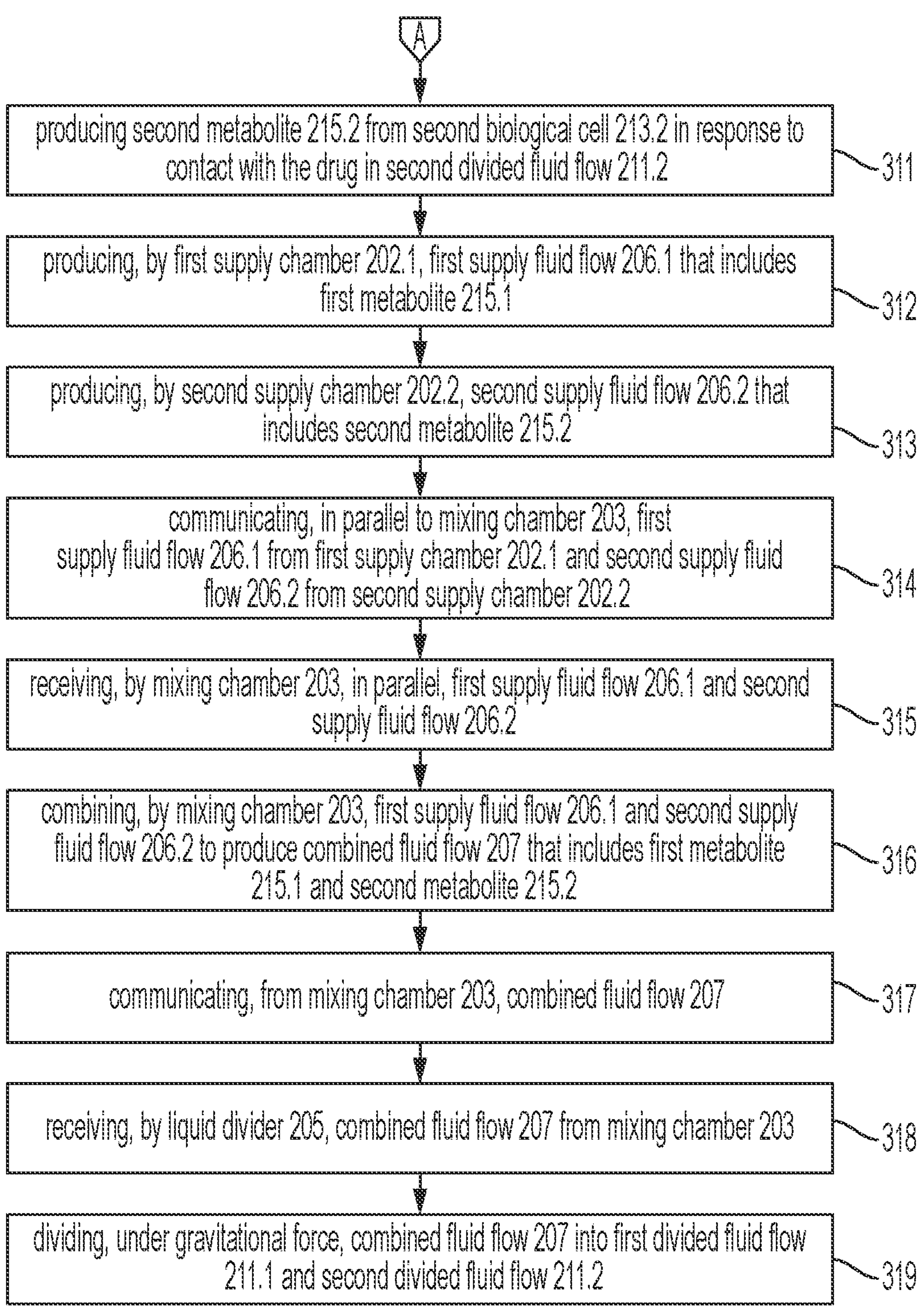
FIG. 12 shows additional steps in determining the physiological response to the drug listed in FIG. 11, according to some embodiments.

Gravity flow micro-physiological article 200 has numerous advantageous and unexpected benefits and uses. In an embodiment, with reference to FIG. 11 and FIG. 12, a process for determining a physiological response to a drug with gravity flow micro-physiological article 200 includes: disposing first biological cell 213.1 in a first supply chamber 202.1 of the gravity flow micro-physiological article 200 (step 300); disposing second biological cell 213.2 in a second supply chamber 202.2 of the gravity flow micro-physiological article 200 (step 301); disposing a blood surrogate 214 in a liquid divider 205 of the gravity flow micro-physiological article 200, the blood surrogate 214 comprising the drug (step 302); subjecting the gravity flow micro-physiological article 200 to movement to divide the blood surrogate 214 into a first divided fluid flow 211.1 and a second divided fluid flow 211.2 of the gravity flow micro-physiological article 200 (step 303), wherein the first divided fluid flow 211.1 and the second divided fluid flow 211.2 independently include a portion of the blood surrogate 214 in a proportionate amount as physically determined by a divider 209 of the gravity flow micro-physiological article 200; communicating the first divided fluid flow 211.1 to the first supply chamber 202.1 (step 304); receiving, by the first supply chamber 202.1, the first divided fluid flow 211.1 from a first return fluid chamber 208.1 of the gravity flow micro-physiological article 200 (step 305); communicating the second divided fluid flow 211.2 to the second supply chamber 202.2 (step 306); receiving, by the second supply chamber 202.2, the second divided fluid flow 211.2 from a second return fluid chamber 208.2 of the gravity flow micro-physiological article 200 (step 307); contacting, in the first supply chamber 202.1, the first biological cell 213.1 with the drug in the first divided fluid flow 211.1 (step 308); producing a first metabolite 215.1 from the first biological cell 213.1 in response to contact with the drug in the first divided fluid flow 211.1 (step 309); contacting, in the second supply chamber 202.2, the second biological cell 213.2 with the drug in the second divided fluid flow 211.2 (step 310); producing a second metabolite 215.2 from the second biological cell 213.2 in response to contact with the drug in the second divided fluid flow 211.2 (step 311); producing, by the first supply chamber 202.1, a first supply fluid flow 206.1 that includes the first metabolite 215.1 (step 312); producing, by the second supply chamber 202.2, a second supply fluid flow 206.2 that includes the second metabolite 215.2 (step 313); communicating, in parallel to a mixing chamber 203, the first supply fluid flow 206.1 from the first supply chamber 202.1 and the second supply fluid flow 206.2 from the second supply chamber 202.2 (step 314); receiving, by the mixing chamber 203, in parallel, the first supply fluid flow 206.1 and the second supply fluid flow 206.2 (step 315); combining, by the mixing chamber 203, the first supply fluid flow 206.1 and the second supply fluid flow 206.2 to produce a combined fluid flow 207 that comprises the first metabolite 215.1 and the second metabolite 215.2 (step 316); communicating, from the mixing chamber 203, the combined fluid flow 207 (step 317); receiving, by the liquid divider 205, the combined fluid flow 207 from the mixing chamber 203 (step 318); and dividing; under gravitational force, the combined fluid flow 207 into the first divided fluid flow 211.1 and the second divided fluid flow 211.2 (step 319), wherein the first divided fluid flow 211.1 and the second divided fluid flow 211.2 independently include the first metabolite 215.1 and the second metabolite 215.2 in a proportionate amount as physically determined by the divider 209 to determine independently the physiological response of the first biological cell 213.1 and the second biological cell 213.2 to the drug.

In an embodiment, determining a physiological response to a drug further includes repeatedly iterating steps 304 to 318. for a select number of times to determine independently the physiological response of the first biological cell 213.1 and the second biological cell 213.2 to the drug.

In an embodiment, the first cell and the second cell independently include a normal cell, diseased cell, or a combination of the foregoing types of cells. In an embodiment, the drug comprises a therapeutic drug. In an embodiment, the blood surrogate includes the drug.

Pharmacokinetics is the study of the action of pharmaceuticals and other biologically active compounds from the time they are introduced into the body until they are eliminated. The sequence of events for an oral drug can include absorption through the various mucosal surfaces, distribution via the blood stream to various tissues, biotransformation in the liver and other tissues, action at the target site, and elimination of drug or metabolites in urine or bile. Pharmacokinetics provides a rational means of approaching the metabolism of a compound in a biological system. Gravity flow micro-physiological article 200 can provide pharmokinetic data at the cellular level for such a drug.

A challenge encountered in drug, environmental, nutritional, consumer product safety, or toxicology studies involves extrapolation of metabolic data and risk assessment from in vitro cell culture assays to animals. Although some conclusions can be drawn with the application of appropriate pharmacokinetic principles, substantial limitations can exist. Conventional screening assays use cells under conditions that may involve uncontrolled factors. The circulatory flow, interaction with other tissues, and other parameters associated with a physiological response may include spurious results in data that are not a direct result from cellular metabolism but from other factors. While in vivo animal models can be used to perform pharmacokinetics (PK) or pharmacodynamics (PD) study, it significantly can increase the cost of the research, and the screening throughput is low. Beneficially, gravity flow micro-physiological article 200 fills a need for a platform under which cells can function in controlled conditions with a target drug in a selected blood surrogate. Accordingly, gravity flow micro-physiological article 200 can be used, e.g., for PK or PD studies, drug screening, development of a disease model of interest, and the like.

Gravity flow micro-physiological article 200 can be configured to mimic physiological conditions or provide a platform for investigating cellular response to a compound or composition in a target motif, e.g., a mammal cell (e.g., a human cell), other animal cell, an insect cell, or a plant cell. Gravity flow micro-physiological article 200 can receive one type of living cells, e.g., one type of tissue cells under certain chemical conditions. Cells from various organs or tissue can include epithelial cells, cardiac cells, liver cell types (e.g., hepatocytes, hepatic stellate cells. Kupffer cells, or liver sinusoidal endothelial cells), kidney cells (e.g., intestinal epithelium, enterocytes, Paneth cells, goblet cells, or neuroendocrine cells), lung airway smooth muscle cells, osteocytes, skin cell types (e.g., keratinocytes, melanocytes, or Langerhans cells), brain cells (e.g., nerve cells or glial cells), gametes, germ cells, endocrine cells, and the like.

In some embodiments, gravity flow micro-physiological article 200 can be configured to represent a functional microenvironment of an organ (e.g., a functional unit or section of an organ, or a tissue-capillary interface) or metabolic condition in which cells can encounter the drug in the blood surrogate. In such embodiments, two different cell types can be disposed in gravity flow micro-physiological article 200. In some embodiments, living human cells can be cultured and transferred into gravity flow micro-physiological article 200 under a physiological condition that can correspond, e.g., to such a physiological condition in a human organ.

It should be appreciated that gravity flow micro-physiological article 200 provides an in vivo model for various applications, e.g., in analysis of drug efficacy, toxicity, or pharmacodynamics, or in studies of diseases or disorders. To this end, gravity flow micro-physiological article 200 can have various designs and configurations that can include fluidics due to movement (e.g., rotation, tilting, and the like) of gravity flow micro-physiological article 200 and the effect of gravity on the fluid compositions (e.g., blood surrogate, drugs, cells, and the like) disposed in the gravity flow micro-physiological article 200 for fluid movement of such fluids inside of gravity flow micro-physiological article 200. Accordingly, gravity flow micro-physiological article 200 can mimic a physiological condition.

In an embodiment, a plurality (e.g., two or more) gravity flow micro-physiological articles 200 can be fluidically connected together when one or more other fluid connector members (e.g., devices, systems, or modules that can perform fluid transfer, filtration, signal detection, or imaging) are present between the gravity flow micro-physiological articles 200. Here, gravity flow micro-physiological articles 200 can be fluidically connected, when the gravity flow micro-physiological articles 200 are indirectly connected, e.g., through a biosensor, a filter, or an analytical instrument (e.g., via tubing), such that a fluid exiting the previous gravity flow micro-physiological article 200 can be communicated to first flow through a biosensor, filter, or analytical instrument, e.g., for detection, analysis, or filtration of the fluid, before it enters a next gravity flow micro-physiological article 200. A portion of the fluid can pass or flow from one gravity flow micro-physiological article 200 to another gravity flow micro-physiological article 200. In an embodiment, a plurality of gravity flow micro-physiological articles 200 can be connected such that a fluid can pass or flow directly from one gravity flow micro-physiological article 200 to another gravity flow micro-physiological article 200 in an absence of intervening components. In such an embodiment, gravity flow micro-physiological articles 200 can be designed or integrated such that the outlet of one gravity flow micro-physiological article 200 and the inlet of another gravity flow micro-physiological article 200 share the same port.

Gravity flow micro-physiological article 200 determines a physiological response to a drug, a biological effect (e.g., toxicity, immune response, metabolic formation, kinetic rate, and the like) of a drug. The drug can include an active agent, and the blood surrogate can include, in addition to the drug, an appropriate medium for metabolic support of certain cells. Gravity flow micro-physiological article 200 can receive the blood surrogate so that cells can be held under conditions of a disease or disorder and subjected to various kinds or dosages of drugs to determine an optimal treatment regimen for the disease or disorder.

Exemplary active agents include proteins, peptides, antigens, antibodies or portions thereof, enzymes, nucleic acids, siRNA, shRNA, aptamers, small molecules, antibiotics, therapeutic agents, molecular toxins, nanomaterials, particulates, or a combination thereof. In some embodiments, gravity flow micro-physiological article 200 is used to evaluate active agents that are effective in treating a disease or disorder but that might be toxic at certain levels.

The blood surrogate also can include other compositional constituents such as saline, plasma, aerosols, environmental contaminants or pollutants (e.g., microorganisms, organic or inorganic contaminants present in food or water, or air pollutants), viruses, bacteria, and the like.

Elements of gravity flow micro-physiological article 200 can be various sizes. It is contemplated that elements of gravity flow micro-physiological article 200 can be have various length, volumes, shapes, and sizes to effect fluid communication in an absence of interference with determining a physiological response to a drug.

Elements of gravity flow micro-physiological article 200 can be made of a material that is physically or chemically resilient in an environment in which gravity flow micro-physiological article 200 is disposed. Exemplary materials include a metal, ceramic, thermoplastic, glass, semiconductor, and the like. The elements of gravity flow micro-physiological article 200 can be made of the same or different material and can be monolithic in a single physical body or can be separate members that are physically joined.

Gravity flow micro-physiological article 200 includes substrate 201 and flow channel 204, supply chamber 202, and divider 209 disposed therein. The number and dimension of flow channel 204, supply chamber 202, and divider 209 can vary depending on the design, dimension, or function of gravity flow micro-physiological article 200. In some embodiments, gravity flow micro-physiological article 200 includes a plurality of such structures (e.g., from two to ten or more). A design and optimum number or dimension of flow channel 204, supply chamber 202, and divider 209 can be selected for a certain application. For example, if assessment of reproducibility or comparison of two conditions is desirable, gravity flow micro-physiological article 200 can be constructed to include from two to five flow channels 204, supply chambers 202, and dividers 209. This can provide for a number of read-outs per flow channel 204, supply chamber 202, and divider 209, e.g., allowing assessment of reproducibility or for validation and implementation of the technology. For example, each supply chamber 202 can run a different condition (e.g., normal (healthy) cells vs. diseased cells, applying different dosages of the same drug, or applying different drugs at the same dosage to different cells).

The dimensions of flow channel 204, supply chamber 202, and divider 209 can each independently vary, e.g., depending on the function (e.g., as a conduit for fluid transfer or as a chamber for monitoring cellular response), flow conditions, cellular microenvironment to be simulated, or methods for detecting cellular response. Thus, the cross-sectional dimensions of flow channel 204, supply chamber 202, and divider 209 independently can be, e.g., from about 1 μm to about 10 cm, or from about 1 μm to about 0.5 cm. A volume of flow channel 204, supply chamber 202, and divider 209 independently can be, e.g., 10 nanoliters to 1 liter, specifically from 100 nL to 100 mL, and more specifically from 10 nL to 50 μL.

In an embodiment, gravity flow micro-physiological article 200 is fabricated from a biocompatible material. Exemplary biocompatible materials include glass, silicons, polyurethanes or derivatives thereof, rubber, molded plastic, polymethylmethacrylate (PMMA), polycarbonate, polytetrafluoroethylene (TEFLON™), polyvinylchloride (PVC), polydimethylsiloxane (PDMS), and polysulfone. According to an embodiment, gravity flow micro-physiological article 200 is fabricated from PDMS (poly-dimethylsiloxane). In some embodiments, gravity flow micro-physiological article 200 is disposable. In some embodiments, gravity flow micro-physiological article 200 is fabricated from material that allows sterilization (e.g., by UV, high temperature or pressure, ethylene oxide, ethanol, and the like) after use.

In some embodiments, the inner surfaces of gravity flow micro-physiological article 200 (e.g., the surfaces of flow channel 204, supply chamber 202, and divider 209) that are in contact with the blood surrogate can be modified for reducing non-specific binding of a species in the blood surrogate to the inner surfaces of gravity flow micro-physiological article 200. For example, at least one surface of the flow channel 204, supply chamber 202, divider 209, or mixing chamber 203 in contact with the blood surrogate can be coated with a surfactant (e.g., PLURONIC® 127) or a blocking protein such as bovine serum albumin, for reducing cell or protein adhesion thereto. Additional surfactant that can be used to reduce the adhesive force between the surface of gravity flow micro-physiological article 200 and non-specific binding of a species in the blood surrogate can include hydrophilic (e.g., amphipathic) polymers and polymeric surface-acting agents; non-ionic agents such as polyhydric alcohol-type surfactants, e.g., fatty acid esters of glycerol, pentaerythritol, sorbitol, sorbitan, and more hydrophilic agents made by their alkoxylation, including polysorbates (TWEEN®); polyethylene glycol-type surfactants such as PLURONIC surfactants (e.g., poloxamers), polyethylene glycol (PEG), methoxypolyethylene glycol (MPEG), polyacrylic acid, polyglycosides, soluble polysaccharides, dextrins, microdextrins, gums, and agar; ionic agents, including anionic surfactants such as salts of carboxylic acids (soaps), sulfuric acids, sulfuric esters of higher alcohols; cationic surfactants such as salts of alkylamine type, quaternary ammonium salts, or amphoteric surfactants such as amino acid type surfactants and betaine type surfactants. The methods or reagents used to reduce non-specific binding of a species in the blood surrogate to the inner surfaces of gravity flow micro-physiological article 200 can be selected based on the material of substrate 201 or types of species to be blocked.

In accordance with the foregoing, it will be appreciated that gravity flow micro-physiological article 200 provides a reliable mufti-organ microphysiological cell culture system that can be used for large-scale drug screening with human primary and stem cells. Moreover, gravity flow micro-physiological article 200 can provide predictive data for drug candidates. Additionally, gravity flow micro-physiological article 200 can be used in drug development for testing of new compounds to save money on clinical trials. Beneficially, gravity flow micro-physiological article 200 overcomes limitation of conventional devices that cannot be used as a human body mimic and that have designs that are expensive to make, difficult to set up, and difficult to operate. Moreover, conventional devices include on-board MEMS components that can fail because they are exposed to liquid full of proteins that foul them and are prone to leaking. Conventional systems also do not capture the complexity of human organs. Gravity flow micro-physiological article 200 provides a fluidic infrastructure for an MPS in an inexpensive, easy-to-set-up, and easy-to-operate format, overcoming the limitation of conventional systems that have hindered adoption of this MPS. Gravity flow micro-physiological article 200 provides adjustment of biological parameters to make MPS mimic the human body more reliably than conventional technology and can test drugs fast and inexpensively to generate data for pharmaceutical studies.

Gravity flow micro-physiological article 200 is open and holds a cell culture medium inside its fluidic channels via surface tension. Gravity drives fluidic flow in gravity flow micro-physiological article 200, and hydraulic resistances control flow rates therein so gravity flow micro-physiological article 200 operates in an absence of a mechanical fluid pump. Because gravity flow micro-physiological article 200 is open, leaking is not an issue.

Gravity flow micro-physiological article 200 as an MPS mimics the human body because gravity flow micro-physiological article 200 can include functional organ volume ratios, involve blood residence times per organ volume, and have a proportion of blood surrogate identical to or substantially equivalent to the human body. In addition, gravity flow micro-physiological article 200 can have a geometry and size of interconnecting fluid channels so that a combination of gravity forces, surface tension, and hydraulic resistances function to provide liquid flow at a physiological flow rate. Gravity flow micro-physiological article 200 can include a silicon chip that controls fluidic flow and a chip support that has low resistance channels for fluid recirculation and can be formed, e.g., microfabricated on a silicon wafer, using contact photolithography, and deep reactive ion etching. The chip support can be 3D-printed.

The flow rates and fluid residence times in various parts of gravity flow micro-physiological article 200 can be determined and compared with measured flow rates against calculations, including an influence of evaporation. Physiological flow rates and fluid residence times can be used with in vitro tissues so that gravity flow micro-physiological article 200 operates as a body mimic.

Gravity flow micro-physiological article 200 produces drug metabolites and recirculates those metabolites among organ mimics. Toxic metabolites reach all tissues. In an exemplary determination of a physiological response to a drug, gravity flow micro-physiological article 200 is loaded with primary tissues, and 5-urofluoracil (5-FU), a cancer prodrug, is added. Cell survival is determined from fluorescent viability dye. It is contemplated that a positive test produces a toxic, cancer-treating metabolite in a liver mimic that affects cancer tissues and regular tissues in other parts of gravity flow micro-physiological article 200.

Advantageously, gravity flow micro-physiological article 200 overcomes leaking, becoming contaminating, or experiencing irregular flow because of air bubbles. The low success rate of conventional closed, pumped systems is a technical impediment of conventional articles to large-scale commercial success of conventional MPS. Gravity flow micro-physiological article 200 overcome those obstacles. Moreover, gravity flow micro-physiological article 200 can perform drug screening in repeated experiments that are performed in parallel to produce statistically sound datasets. Human actions add variation to data, and gravity flow micro-physiological article 200 reduces human intervention so that data taken from gravity flow micro-physiological article 200 may be more reliable than for conventional systems that involve more human interaction with loading, controlling, and sampling of conventional systems.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix (s) as used herein is intended to include both the singular and the plural of the term that it modifies, thereby including at least one of that term (e.g., the colorant(s) includes at least one colorants). Option, optional, or optionally means that the subsequently described event or circumstance can or cannot occur, and that the description includes instances where the event occurs and instances where it does not. As used herein, combination is inclusive of blends, mixtures, alloys, reaction products, collection of elements, and the like.

As used herein, a combination thereof refers to a combination comprising at least one of the named constituents, components, compounds, or elements, optionally together with one or more of the same class of constituents, components, compounds, or elements.

All references are incorporated herein by reference.

The use of the terms "a," "an," and "the" and similar referents in the context of describing the invention (especially in the context of the following claims) are to be construed to cover both the singular and the plural, unless otherwise indicated herein or clearly contradicted by context. It can further be noted that the terms first, second, primary, secondary, and the like herein do not denote any order, quantity, or importance, but rather are used to distinguish one element from another. It will also be understood that, although the terms first, second, etc. are, in some instances, used herein to describe various elements, these elements should not be limited by these terms. For example, a first current could be termed a second current, and, similarly, a second current could be termed a first current, without departing from the scope of the various described embodiments. The first current and the second current are both currents, but they are not the same condition unless explicitly stated as such.

The modifier about used in connection with a quantity is inclusive of the stated value and has the meaning dictated by the context (e.g., it includes the degree of error associated with measurement of the particular quantity), The conjunction or is used to link objects of a list or alternatives and is not disjunctive; rather the elements can be used separately or can be combined together under appropriate circumstances.

What is claimed is:

1. A gravity flow micro-physiological article for determining a physiological response to a drug, the gravity flow micro-physiological article comprising: a substrate; a first supply chamber disposed on the substrate configured to contain a first fluid volume and to direct a first supply fluid flow; a second supply chamber disposed on the substrate configured to contain a second fluid volume and to direct a second supply fluid flow, such that the first supply fluid flow from the first supply chamber is parallel to the second supply fluid flow from the second supply chamber; a mixing chamber in fluid communication with the first supply chamber and the second supply chamber the mixing chamber defining a unitary internal volume structurally arranged to: receive the first supply fluid flow from the first supply chamber; receive the second supply fluid flow from the second supply chamber; and combine the first supply fluid flow and the second supply fluid flow to form a combined fluid flow within the unitary internal volume; a liquid divider in fluid communication with the mixing chamber, wherein the liquid divider comprises a physical divider wall disposed therein that structurally partitions the liquid divider into a first return path and a second return path: wherein the liquid divider: receives the combined fluid flow from the mixing chamber; and divides the combined fluid flow via the physical divider wall into a first divided fluid flow and a second divided fluid flow, wherein the liquid divider is in fluid communication with the first supply chamber and the second supply chamber such that: the first supply chamber receives the first divided fluid flow from the liquid divider; and the second supply chamber receives the second divided fluid flow from the liquid divider; and a plurality of flow channels fluidically interconnecting the supply chambers, the mixing chamber, and the liquid divider, and providing fluid flow therebetween, such that the combined fluid flow is recirculated through the flow channels and returned to at least one of the supply chambers in an absence of a fluidic actuator or pump, wherein the first supply chamber, the second supply chamber, the mixing chamber, and the flow channels are open and directly exposed to the atmosphere; and the gravity flow micro-physiological article communicates fluid among the first supply chamber, the second supply chamber, the mixing chamber, and the flow channels due to gravity as the gravity flow micro-physiological article does not comprise a fluidic actuator or a pump.

2. The gravity flow micro-physiological article of claim 1, wherein the liquid divider comprises a divider that partitions the liquid divider into a plurality of return fluid chambers.

3. The gravity flow micro-physiological article of claim 2, a number of the return fluid chambers in the plurality of return fluid chambers is equal to a number of supply chambers disposed on the substrate.

4. The gravity flow micro-physiological article of claim 1, wherein the first supply chamber receives a first biological cell; the second supply chamber receives a second biological cell; and the liquid divider receives a blood surrogate comprising the drug.

5. The gravity flow micro-physiological article of claim 4, wherein the gravity flow micro-physiological article divides the blood surrogate into a first divided fluid flow and a second divided fluid flow in response to the gravity flow micro-physiological article being subjected to movement, wherein the first divided fluid flow and the second divided fluid flow independently comprise a portion of the blood surrogate in a proportionate amount as physically determined by the divider.

6. The gravity flow micro-physiological article of claim 5, wherein the gravity flow micro-physiological article communicates the first divided fluid flow to the first supply chamber; the first supply chamber receives the first divided fluid flow from the first return fluid chamber; the gravity flow micro-physiological article communicates the second divided fluid flow to the second supply chamber; and the second supply chamber receives the second divided fluid flow from the second return fluid chamber of the gravity flow micro-physiological article.

7. The gravity flow micro-physiological article of claim 6, wherein, in the first supply chamber, the first biological cell contacts the drug in the first divided fluid flow, so that a first metabolite is produced by the first biological cell in response to contact with the drug in the first divided fluid flow; and, in the second supply chamber, the second biological cell contacts the drug in the second divided fluid flow, so that a second metabolite is produced by the second biological cell in response to contact with the drug in the second divided fluid flow.

8. The gravity flow micro-physiological article of claim 7, wherein the first supply chamber produces a first supply fluid flow that comprises the first metabolite; the second supply chamber produces a second supply fluid flow that comprises the second metabolite; and the first supply fluid flow from the first supply chamber and the second supply fluid flow from the second supply chamber are communicated in parallel to the mixing chamber.

9. The gravity flow micro-physiological article of claim 8, wherein the mixing chamber receives, in parallel, the first supply fluid flow and the second supply fluid flow; combines the first supply fluid flow and the second supply fluid flow; produces a combined fluid flow that comprises the first metabolite and the second metabolite; and communicates the combined fluid flow to the liquid divider.

10. The gravity flow micro-physiological article of claim 9, wherein the liquid divider receives the combined fluid flow from the mixing chamber; and divides, under gravitational force, the combined fluid flow into the first divided fluid flow and the second divided fluid flow, such that the first divided fluid flow and the second divided fluid flow independently comprise the first metabolite and the second metabolite in a proportionate amount as physically determined by the divider.

11. The gravity flow micro-physiological article of claim 4, wherein the first cell and the second cell independently comprise a normal cell, diseased cell, or a combination of the foregoing types of cells.

12. The gravity flow micro-physiological article of claim 4, wherein the drug comprises a therapeutic drug.

* * * * *